United States Patent
Richard et al.

(10) Patent No.: US 12,105,001 B2
(45) Date of Patent: Oct. 1, 2024

(54) DEVICE FOR DETECTING THE PRESENCE OF POLLEN IN THE AIR, AND CORRESPONDING DETECTION METHOD

(71) Applicants: LIFY AIR, Orléans (FR); CENTRE NATIONAL LA RECHERCHE SCIENTIFIQUE, Paris (FR); UNIVERSITE D'ORLEANS, Orléans (FR)

(72) Inventors: Jérôme Richard, Saint Denis en Val (FR); Johann Lauthier, Saint Jean de Braye (FR); Jean-Baptiste Renard, Orléans (FR)

(73) Assignees: LIFY AIR, Orléans (FR); CENTRE NATIONAL DE LA RECHERCHE SCIENTIFIQUE, Paris (FR); Universite D'Orleans, Orléans (FR)

( * ) Notice: Subject to any disclaimer, the term of this patent is extended or adjusted under 35 U.S.C. 154(b) by 278 days.

(21) Appl. No.: 17/789,611

(22) PCT Filed: Dec. 21, 2020

(86) PCT No.: PCT/FR2020/000283
§ 371 (c)(1),
(2) Date: Jun. 28, 2022

(87) PCT Pub. No.: WO2021/136889
PCT Pub. Date: Jul. 8, 2021

(65) Prior Publication Data
US 2023/0035280 A1    Feb. 2, 2023

(30) Foreign Application Priority Data
Dec. 30, 2019 (FR) .................................. 1915708

(51) Int. Cl.
*G01N 15/06* (2024.01)
*G01N 15/00* (2024.01)
(Continued)

(52) U.S. Cl.
CPC ......... *G01N 15/06* (2013.01); *G01N 15/0211* (2013.01); *G01N 21/53* (2013.01);
(Continued)

(58) Field of Classification Search
CPC ........... G01N 33/0004; G01N 33/0009; G01N 33/0027; G01N 33/0031; G01N 33/0034;
(Continued)

(56) References Cited

U.S. PATENT DOCUMENTS 6,594,001 B1 * 7/2003 Yabusaki ........... G01N 15/1459
356/73
7,119,900 B2 * 10/2006 Okumura ........... G01N 15/0211
356/364
(Continued)

FOREIGN PATENT DOCUMENTS

CN    103454203 A  * 12/2013
CN    106018193 A    10/2016
(Continued)

OTHER PUBLICATIONS

C. Benoit et al., "All-Optical Automatic Pollen Identification: Towards an Operational System" Atmospheric Environment, Pergamon, GB, vol. 140, Jun. 2, 2016; pp. 202-212.

*Primary Examiner* — Gordon J Stock, Jr.
(74) *Attorney, Agent, or Firm* — Greer, Burns & Crain, Ltd.

(57) ABSTRACT

A device for detecting the presence of pollen in the air, including a measuring chamber isolated from external light, an arrangement configured to drive an air flow through the measuring chamber, and a light source emitting a light beam
(Continued)

in a direction of propagation through the air flow, into the measuring chamber. The device includes at least four photosensitive sensors configured to measure the luminous flux diffused by the illuminated air flow, in four different directions, a clock, at least two meteorological sensors, and at least one computer capable of determining the nature of a pollen particle present in the air from the data measured by the photosensitive sensors, the clock and the meteorological sensors.

10 Claims, 5 Drawing Sheets

(51) Int. Cl.
  *G01N 15/0205* (2024.01)
  *G01N 15/075* (2024.01)
  *G01N 21/47* (2006.01)
  *G01N 21/53* (2006.01)
  *G01N 33/00* (2006.01)

(52) U.S. Cl.
  CPC . *G01N 33/0031* (2013.01); *G01N 2015/0046* (2013.01); *G01N 2015/0238* (2013.01); *G01N 15/075* (2024.01); *G01N 2021/4711* (2013.01); *G01N 2021/4733* (2013.01)

(58) Field of Classification Search
  CPC .............. G01N 33/0036; G01N 15/02; G01N 15/0205; G01N 15/0211; G01N 15/06; G01N 15/075; G01N 15/10; G01N 15/14; G01N 15/149; G01N 2015/0038; G01N 2015/0042; G01N 2015/0046; G01N 2015/019; G01N 2015/0238; G01N 2015/025; G01N 2015/0277; G01N 2015/0288; G01N 2015/0294; G01N 2015/03; G01N 2015/035; G01N 2015/1493; G01N 2015/1495; G01N 2015/1497; G01N 21/47; G01N 21/4738; G01N 21/49; G01N 21/51; G01N 21/53; G01N 2021/4704; G01N 2021/4711; G01N 2021/4714; G01N 2021/4733; G01N 2021/4764; G01N 2021/4769
  See application file for complete search history.

(56) References Cited

U.S. PATENT DOCUMENTS

| | | | | |
|---|---|---|---|---|
| 9,244,010 B2* | 1/2016 | Wagner | ................... | G01N 21/53 |
| 9,759,736 B2* | 9/2017 | Zamama | ................... | G01S 17/95 |
| 9,958,376 B2* | 5/2018 | Nakai | ................ | G01N 15/1434 |
| 11,262,286 B2* | 3/2022 | Ozcan | ................... | G03H 1/2645 |
| 2001/0029535 A1* | 10/2001 | Hirano | ................... | H04L 67/02 |
| | | | | 709/224 |
| 2004/0066513 A1 | 4/2004 | Okumura et al. | | |
| 2021/0247289 A1* | 8/2021 | Enokido | ............ | G01N 33/0075 |

FOREIGN PATENT DOCUMENTS

| | | | | |
|---|---|---|---|---|
| CN | 106979909 A | * | 7/2017 | ......... G01N 15/0205 |
| EP | 1281951 A1 | | 2/2003 | |
| EP | 3392644 A1 | | 10/2018 | |
| EP | 3413034 A1 | | 12/2018 | |
| JP | 2004184395 A | * | 7/2004 | |
| JP | 2008216133 A | * | 9/2008 | |

\* cited by examiner

DEVICE FOR DETECTING THE PRESENCE OF POLLEN IN THE AIR, AND CORRESPONDING DETECTION METHOD

CROSS-REFERENCES TO RELATED APPLICATIONS

This application claims the benefit of the International Application No. PCT/FR2020/000283, filed on Dec. 21, 2020, and of the French patent application No. 1915708 filed on Dec. 30, 2019, the entire disclosures of which are incorporated herein by way of reference.

FIELD OF THE INVENTION

The present invention relates to a device for detecting the presence of pollen in the air.

The invention also relates to a method for detecting the presence of pollen in the air.

BACKGROUND OF THE INVENTION

When particles, or grains, of pollen are disseminated in the air, they constitute a major cause of allergic reaction. For sensitive people, they can thus cause symptoms generally taking the form of allergic rhinitis, often accompanied by conjunctivitis. Such allergic reactions can be extremely harmful to people who experience them. In addition, they can lead to the onset of asthma in these people.

People with allergies are not sensitive to all types of pollen. Generally, a person can be sensitive to one type of pollen, or to several types. In France, the pollen of certain trees, such as birch, cypress, ash or hazel, certain grasses such as cereals or orchard grass, or even certain herbaceous plants such as sorrel or ragweed, are, in particular, known to trigger allergic reactions in sensitive individuals.

For sensitive people, it is particularly useful to know the places and the periods where pollen appears that triggers allergic reactions in them. This knowledge allows them to take measures to reduce the risk of an allergic reaction, such as measures to avoid the concerned areas, containment inside buildings when the air contains too high a concentration of the pollen in question, wearing a breathing mask, taking preventive medication such as an antihistamine, etc.

To enable them to obtain this information, there are calendars allowing them to know, approximately, the periods of dissemination of each pollen, and maps allowing to know the zones in which these types of pollen appear. However, these data are very imprecise. There are also sensors intended to determine the concentration of pollen particles in the air during a determined period. The most commonly used sensors are either gravimetric or volumetric.

So-called gravimetric devices are thus known, which collect the pollen grains that are deposited by gravity on a horizontal support. These devices, for example of the "Durham" type, have a relatively low recovery efficiency. Consequently, their measurements are deemed to be inaccurate, especially when they relate to relatively short measurement periods.

Also known are so-called volumetric devices, for example of the "Hirst" type, in which a flow of air is projected onto an adhesive support, the particles contained in the air sticking to this adhesive support. It is then possible to observe the pollen particles thus trapped by optical microscopy.

In other devices, known as "Cour" devices, an air flow passes through a filter that collects pollen particles. The filter is then dissolved in the laboratory in order to observe the pollen by optical microscopy.

Such devices, which constitute the reference measurement equipment to date, require numerous manipulations. Thus, the adhesive support or the filter having collected the pollen particles must be checked regularly and then be analyzed in the laboratory. The accuracy of the measurements depends on the frequency of the readings, and the result for a given period can only be obtained several hours after the end of this period.

The pollen measurements obtained by such methods therefore do not make it possible to provide sensitive persons with truly relevant information to enable them to avoid an allergic attack. Indeed, these people can only obtain information concerning the appearance of pollen in the air several hours after this appearance, and therefore most often after their allergic reaction has been triggered. The lack of real-time information on the presence of pollen in the air is therefore detrimental for these sensitive people.

Many other methods of measuring the pollen concentration in the air have been proposed. However, they have drawbacks, such as high cost or bulk of the necessary apparatus, difficulty in discriminating the types of pollen observed, or even a long delay between the observation period and the obtaining of the results. These alternative methods are therefore little used.

Because of these difficulties in detecting and measuring the pollen particles present in the air, the geographical density of the measurement points is very low, and the results are only known long after the measurement period. The information obtained is therefore not very usable by sensitive people.

SUMMARY OF THE INVENTION

The present invention aims to overcome these drawbacks of the prior art.

In particular, the aim of the invention is to provide a pollen detection device allowing reliable, efficient and rapid detection and measurement of the pollen particles present in the air.

According to at least some of its embodiments, the invention also aims to provide such a device that makes it possible to carry out a precise measurement of the quantity of each type of pollen present in the air.

The invention also aims to provide such a device that makes it possible to identify the types of pollen present in the air with increased reliability.

In at least some of the embodiments, the invention also aims to allow the amount of pollen present in the air at a given point to be communicated to users, within a very short time after the measurement thereof.

In a particular embodiment, the invention also aims to provide such a device that allows the presence of pollen in the air to be predicted at a given point.

The invention also aims to provide a method for detecting the presence of pollen in the air, which makes it possible to carry out such detection more quickly and efficiently than the known methods.

These objectives, as well as others that will appear more clearly subsequently, are achieved using a device for detecting the presence of pollen in the air, comprising a measuring chamber isolated from external light, means for driving an air flow through this measuring chamber, and a light source emitting a light beam in a direction of propagation through the air flow, into the measuring chamber, this device comprising, according to the invention, at least four photosensitive sensors capable of measuring the luminous flux diffused by the illuminated air flow, including:
- a first sensor measuring the luminous flux diffused in a direction forming an angle of between 5° and 25° with the direction of propagation;
- a last sensor measuring the luminous flux diffused in a direction forming an angle of between 150° and 175° with the direction of propagation;
- at least two sensors each measuring the luminous flux diffused in a direction forming an angle of between 25° and 150° with the direction of propagation;
- the device also comprising a clock, at least two meteorological sensors, and at least one computer capable of determining the nature of a pollen particle present in the air from the data measured by the photosensitive sensors, the clock and the meteorological sensors.

Such a device makes it possible to perform reliable, efficient and almost instantaneous detection of pollen particles in the air. It is also relatively easy to manufacture and inexpensive, which makes it possible to equip a large number of sites with it.

Advantageously, the device comprises four photosensitive sensors capable of measuring the luminous flux diffused by the illuminated air flow.

These four sensors are sufficient to obtain the measurements making it possible to satisfactorily recognize the majority of the pollen known to be capable of triggering allergies. A device comprising these four sensors can therefore, for a moderate cost, detect the presence of pollen grains in the air in real time, and identify the type of each pollen grain.

Advantageously, the first sensor measures the luminous flux diffused in a direction forming an angle comprised between 5° and 20° with the direction of propagation.

Advantageously, the last sensor measures said luminous flux diffused in a direction forming an angle comprised between 150° and 160° with the direction of propagation.

These choices of angles are in fact those that have been identified as allowing the most useful measurements for pollen detection.

According to a preferred embodiment, the device comprises a database comprising luminous flux data diffused by pollen of different types, the computer being able to compare this data with the luminous fluxes measured by the photosensitive sensors.

Preferably, the meteorological sensors comprise at least two sensors chosen from:
- a thermometer,
- a barometer,
- a hygrometer,
- an anemometer,
- a rain gauge, and
- a light sensor.

Advantageously, the meteorological sensors comprise at least:
- a thermometer,
- a barometer,
- a hygrometer.

The choice of these three meteorological sensors indeed allows effective measurement of the meteorological parameters, while limiting the complexity and the cost of the device.

Advantageously, the device comprises a database comprising data relating to the probability of the appearance of pollen as a function of the date and meteorological parameters, and the computer is capable of comparing this data with the data measured by the clock and the meteorological sensors.

Advantageously, the device comprises at least one geolocation device and a database comprising data concerning the probability of the appearance of pollen as a function of geolocation, the computer being able to take geolocation into account to determine the nature of a pollen particle.

The invention also relates to a method for detecting the presence of pollen in the air, comprising:
- a step of illuminating an air flow circulating in a measuring chamber, by a luminous flux oriented in a direction of propagation;
- a step of measuring the luminous flux diffused by the illuminated air flow, in at least four directions, including a direction forming an angle of between 5° and 25° with the direction of propagation, a direction forming an angle of between 150° and 175° with the direction of propagation, and at least two directions each forming an angle of between 25° and 150° with the direction of propagation;
- a step of determining, by a computer, the nature of a pollen particle present in the air flow, from the diffused luminous flux data measured in the measuring step, dating data and meteorological data.

BRIEF DESCRIPTION OF THE DRAWINGS

The invention will be better understood on reading the following description of preferred embodiments, given by way of a simple figurative and non-limiting example, and accompanied by figures including.

DETAILED DESCRIPTION OF THE PREFERRED EMBODIMENTS

Figure 1:
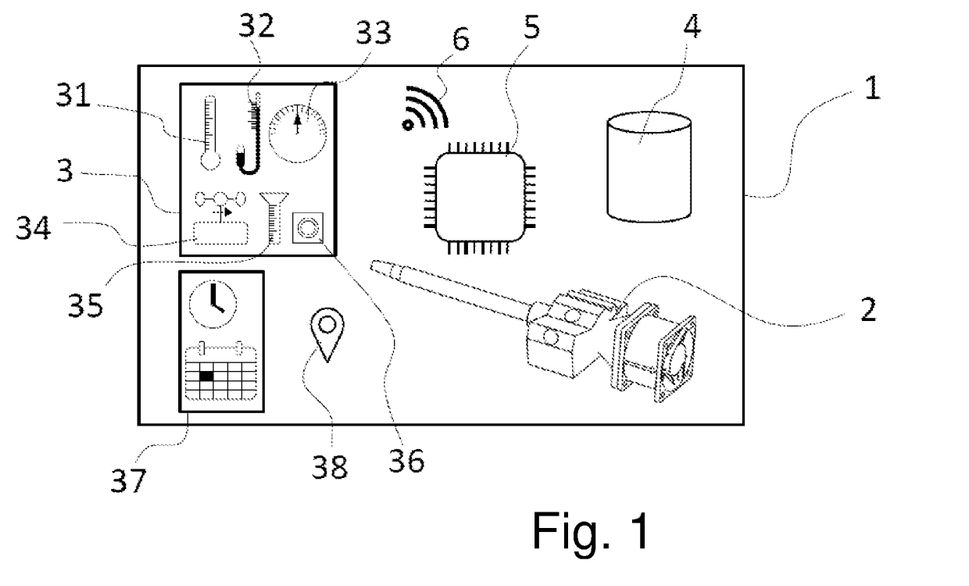
FIG. 1 is a schematic illustration of a pollen detection device according to one embodiment of the invention.

FIG. 1 is a schematic illustration of a device for detecting the presence of pollen in the air according to one embodiment of the invention. This device 1 comprises several components, and, in particular, a pollen detector 2, capable of detecting and measuring the presence of pollen grains in the air. It also comprises a set 3 of meteorological sensors, a clock 37, geolocation equipment 38, a database 4, a computer 5 and a transmission module 6.

Figure 2:
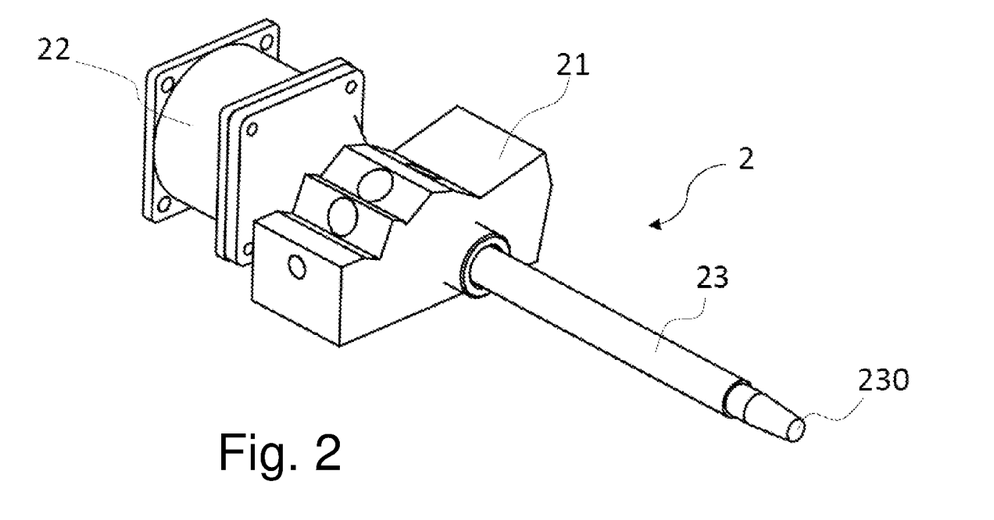
FIG. 2 is a perspective view of the pollen detector of the device shown in FIG. 1.
Figure 3:
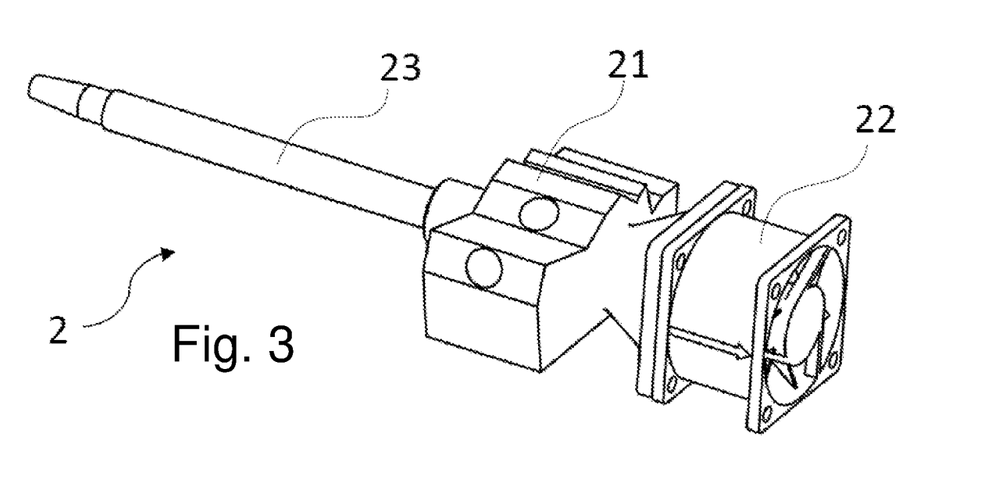
FIG. 3 is another perspective view of the pollen detector shown in FIG. 2.
Figure 4:
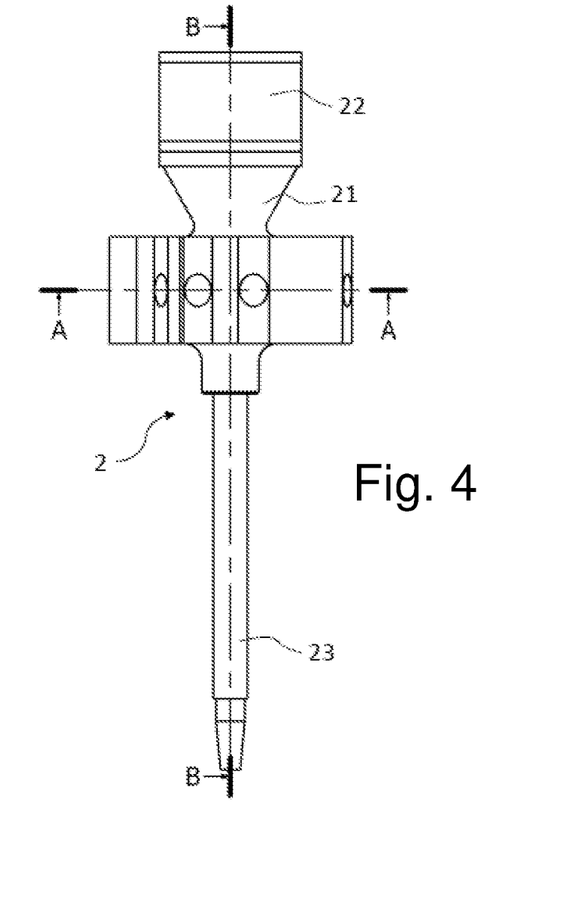
FIG. 4 is a top view of the pollen detector shown in FIG. 2.
Figure 5:
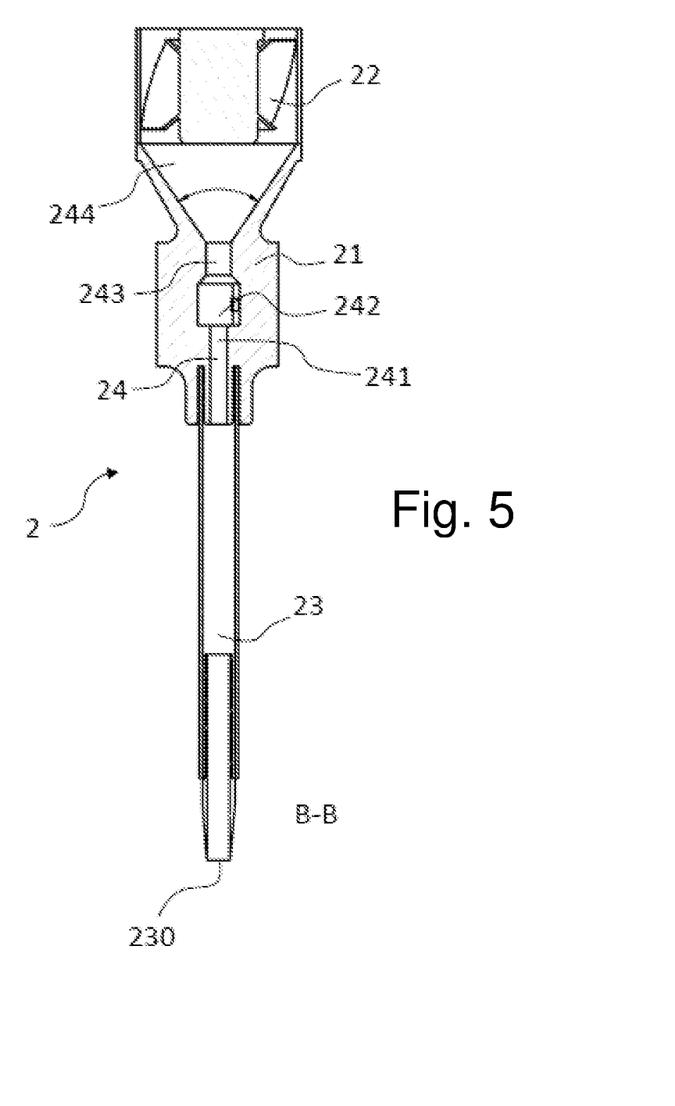
FIG. 5 is a longitudinal section of the pollen detector shown in FIG. 2.
Figure 6:
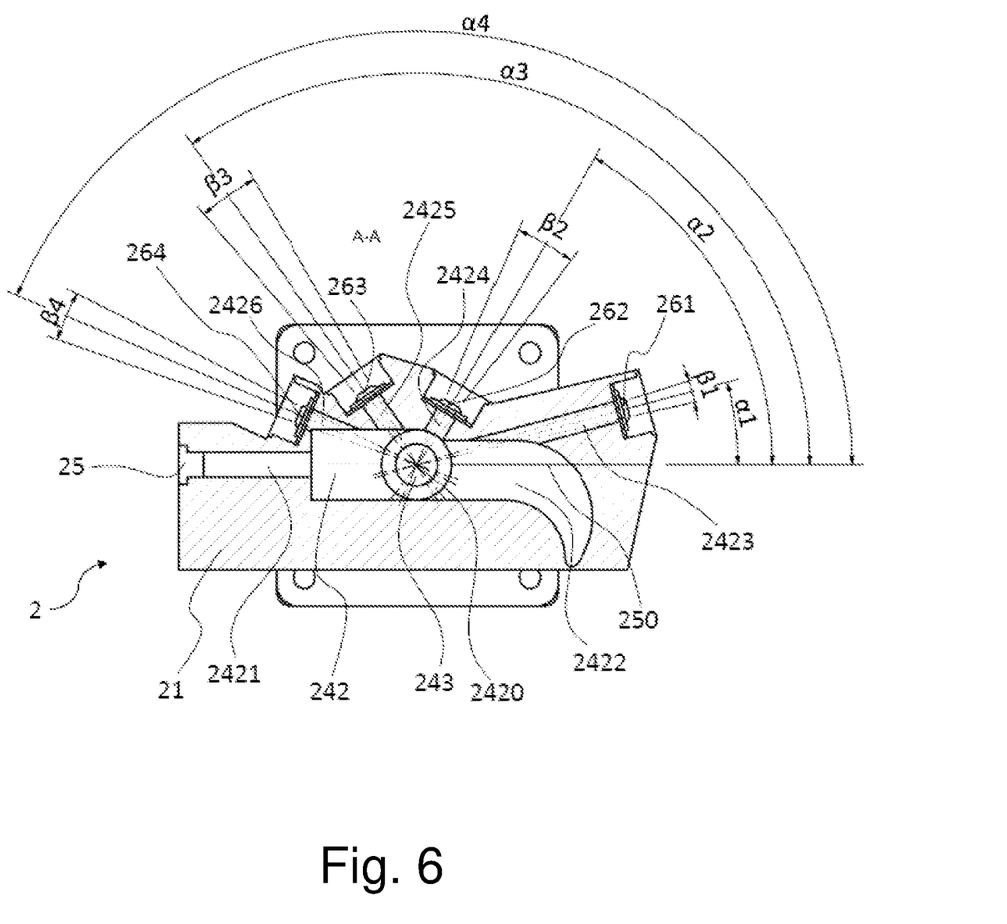
FIG. 6 is a cross-section of the pollen detector shown in FIG. 2.

The pollen detector 2 is shown, in different orientations, by FIGS. 2 to 4, and in sectional view by FIGS. 5 and 6.

This detector 2 comprises a measuring housing 21 that is equipped, at one of its ends, with a suction pump 22 and, at the other of its ends, with a suction pipe 23. The suction pump 22 and the suction pipe 23 are mounted at both ends of an internal pipe 24 of the measuring housing 21. Thus, the suction pump 22 can create a depression in this internal pipe 24 and in the suction pipe 23 so that the ambient air is sucked in by the open end 230 of the suction pipe 23, and crosses the suction pipe 23 and the internal pipe 24 of the measuring housing 21 before being forced out of the pollen detector 2 by the pump 22.

Advantageously, in the embodiment shown, the measuring housing 21 is in one piece. It is therefore produced by an additive manufacturing method. This configuration makes it possible to prevent this measuring housing 21 from being crossed by a section plane, which could generate a risk of introduction into the internal pipe 24 of light that could interfere with the measurements.

FIG. 5 is a longitudinal sectional view of the detector 2, which shows the internal pipe 24 of the measuring housing 21. This internal pipe comprises a substantially cylindrical inlet portion 241, which opens onto the suction pipe 23 at one of its ends. At the second end of this inlet portion 241, the internal pipe 24 comprises a measuring chamber 242. A substantially cylindrical outlet portion 243 opens onto the measuring chamber 242, opposite the inlet portion 241.

Between the outlet portion 243 and the suction pump 22, the internal pipe takes the form of a conical portion 244, one end of which has the diameter of the suction pump 22 and the other end of which has the diameter of the outlet pipe 243. Preferably, the suction pipe 23 and all the portions of the internal pipe 24, with the exception of the measuring chamber 242, are centered on the same longitudinal axis, subsequently called the longitudinal axis of the internal pipe 24.

Preferably, the suction pump 22 draws air so as to give it a rapid velocity in the inlet portion 241 and in the measuring chamber 242. Thus, in the embodiment shown, the suction pump 22 is configured to pump between 0.5 m³ and 1 m³ of air per hour.

The inlet portion 241 has a relatively small diameter, 4 mm in the embodiment shown, in order to impart a relatively high speed to the air circulating in this inlet portion 241 and in the measuring chamber 242.

The outlet portion 243 has a diameter slightly greater than that of the inlet portion 241, 6 mm in the embodiment shown, in order to facilitate the passage through this outlet portion 243 of the particles present in the air circulating in the internal pipe 24, and to prevent these particles from remaining trapped in the measuring chamber 242.

The arrangement of the suction equipment and of the internal pipe 24 of the measuring housing 21 therefore allows the measuring chamber 242 to be crossed by a flow of rapidly circulating air, this air flow being substantially part of a cylinder with a diameter less than 6 mm.

The measuring housing 21 is advantageously equipped to optically analyze the particles contained in this air flow passing through the measuring chamber 242.

FIG. 6 is a cross-sectional view of the detector 2, along a plane transverse to the longitudinal axis of the internal pipe 24 and passing through the measuring chamber 242. This measuring chamber 242 is organized around a measuring point 2420, which corresponds to the intersection between the longitudinal axis of the internal pipe 24 and the measuring plane, corresponding to the section plane of FIG. 6, on which the measuring instruments are aligned.

Several orifices are provided in the measuring chamber 242 to receive the measuring equipment. Thus, a first cylindrical orifice 2421, whose axis is aligned with the measuring plane and with the measuring point 2420, is intended to receive a laser emitter 25, constituting a light source emitting a light beam in a direction of propagation 250 centered on the measuring point 2420, to illuminate the air flow passing through the measuring chamber 242. Preferably, the aperture of this light beam is chosen so that it illuminates the entire width of the air flow passing through the chamber 242.

At its end opposite the cylindrical orifice 2421, the measuring chamber 242 has a closed orifice 2422, shaped to constitute a light trap. This light trap ensures that the light beam emitted by the laser emitter 25 does not interfere with the other components of the measuring housing 21, after it has illuminated the air flow passing through the chamber 242.

The measuring chamber 242 also has four cylindrical measuring orifices, the axes of which are included in the measuring plane and intersect at the measuring point 2420. Each of these measuring orifices has a precise orientation, measured in FIG. 6 with respect to the direction of propagation 250 of the laser beam, which corresponds to the axis of the orifice 2421. Thus, the axis of a first measuring orifice 2423, at the end of which a photosensitive sensor 261 is placed, forms an angle $\alpha 1=15°$ with the direction of propagation 250;

the axis of a second measuring orifice 2424, at the end of which a photosensitive sensor 262 is placed, forms an angle $\alpha 2=60°$ with the direction of propagation 250;

the axis of a third measuring orifice 2425, at the end of which a photosensitive sensor 263 is placed, forms an angle $\alpha 3=125°$ with the direction of propagation 250;

the axis of a fourth measuring orifice 2426, at the end of which a photosensitive sensor 264 is placed, forms an angle $\alpha 4=157°$ with the direction of propagation 250.

Furthermore, each of these measuring orifices has dimensions chosen so as to offer a determined angular opening, starting from the measuring point 2420 to the end of the measuring orifice, which is covered by the photosensitive sensor. This angular opening, around the axis of the measuring orifice, is chosen so that the photosensitive sensor simultaneously captures the light emitted in a determined angular range. Thus, the measuring orifice 2423 is dimensioned such that the photosensitive sensor 261 picks up the light diffused over an angular opening range $\beta 1=4.4°$ and centered on the angle $\alpha 1$;

the measuring orifice 2424 is dimensioned such that the photosensitive sensor 262 picks up the light diffused over an angular opening range $\beta 2=13.5°$ and centered on the angle $\alpha 2$;

the measuring orifice 2425 is dimensioned such that the photosensitive sensor 263 picks up the light diffused over an angular opening range $\beta 3=10.6°$ and centered on the angle $\alpha 3$;

the measuring orifice 2426 is dimensioned such that the photosensitive sensor 264 picks up the light diffused over an angular opening range $04=7.5°$ and centered on the angle $\alpha 4$.

It should be noted that, in other possible embodiments of the invention, the angular position of the various measuring orifices may vary. It is, however, important for a first measuring orifice to be centered on a direction forming a small angle with the direction of propagation, preferably between 5° and 25°, and more advantageously between 5° and 20°, and for a last measurement orifice to be centered on a direction forming a large angle with the direction of propagation, preferably comprised between 150° and 175° and more advantageously comprised between 150° and 160°.

Between these two measuring orifices, at least two other measuring orifices must be positioned at different angular positions with respect to the direction of propagation. The angular positions of these measuring orifices, and therefore of the photosensitive sensors, can, however, be different from those that are shown in FIG. 6.

In the embodiment shown, the measuring chamber 242 has four photosensitive sensors. It is also possible to implement a detector in which the measuring chamber comprises more than four photosensitive sensors, for example five photosensitive sensors. In this case, three orifices comprising photosensitive sensors are placed at various angular positions between the first orifice centered on a direction forming an angle of between 5° and 25° with the direction of propagation, and the last orifice centered on a direction forming an angle of between 150° and 175° with the direction of propagation.

The inventors have, however, determined that the choice of a measuring chamber comprising four photosensitive sensors, each measuring the light emitted in a direction forming a different angle with the direction of propagation, constitutes the most advantageous compromise. These photosensitive sensors are indeed sufficient, in a large number of situations, for their measurements to be able to identify the pollen particles. A larger number of photosensitive sensors can provide more accurate measurements, but only provide relatively small improvements in pollen identification. In contrast, installing a greater number of photosensitive sensors significantly increases the complexity, and therefore the cost, of the pollen detector.

When the detector 2 is in operation, the laser emitter 25 emits a light beam, in the direction of propagation 250, that illuminates the air flow passing through the measuring chamber 242. When this air flow contains no particles, it is transparent and the entire laser beam ends its trajectory in the light trap constituted by the orifice 2422.

When the air flow contains a particle, it is briefly illuminated by the light beam as it passes close to the measuring point 2420. When it is illuminated, this particle will diffuse the light it receives in different directions. The light flux emitted during this diffusion varies according to the emission angle, or diffusion angle, which is measured relative to the direction of propagation of the illuminating laser beam.

This light flux is variable according to various criteria, including the power of the illumination by the laser beam, the wavelength of this illumination, the shape of the illuminated particle, the color of the illuminated particle, the size of the illuminated particle, the surface state of the illuminated particle, the opacity of the illuminated particle, the reflective character of the illuminated particle, etc.

Figure 7:
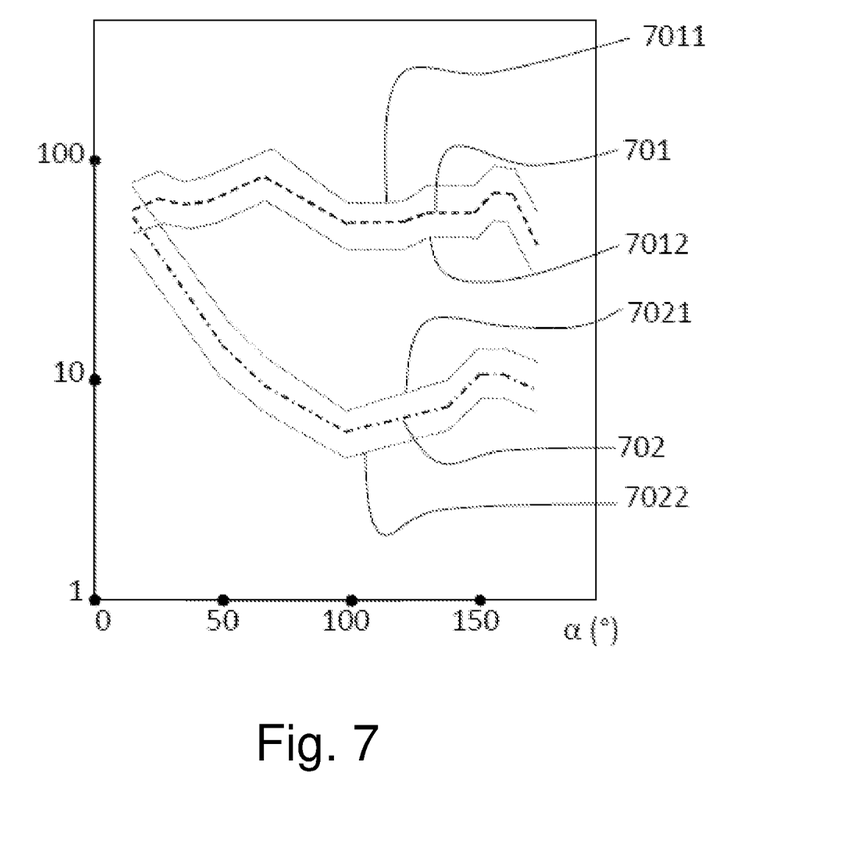
FIG. 7 is a plot showing the light diffused by two illuminated pollen particles, as a function of the diffusion direction.

The inventors have observed that, for the same illumination, the different types of particles diffuse a distinct luminous flux as a function of the angle of diffusion. Thus, by way of example, FIG. 7 is a curve representing the luminous flux diffused by two different particles, subjected to the same illumination, as a function of the angle of diffusion. Curve 701 thus represents the luminous flux diffused by a first particle, which is a fir pollen particle, and curve 702 represents the flux diffused by a second particle, which is a corn pollen particle.

In this figure, the x-axis represents the diffusion angles α, in which each particle emits diffused light when it is illuminated. The y-axis represents the luminous flux emitted by each particle in each of these directions. This axis is a logarithmic axis, graduated in an arbitrary unit. It should be noted that, for each particle, the flux value is normalized so as to present a value identical to 15°. Curves 7011 and 7012 represent the measurement uncertainties corresponding to curve 701, and curves 7021 and 7022 represent the measurement uncertainties corresponding to curve 702.

The inventors have thus analyzed the light diffusion of a large number of particles likely to be present in the air, and, in particular, of the most commonly observed pollen particles. They observed that the light diffusion curves, produced with equipment configured to give comparable results, were generally distinct according to the type of illuminated particles, and similar for illuminated particles of the same type. Thus, the diffusion curve 701 of the fir pollen is very different from the curve 702 of the corn pollen.

For example, a pollen particle from a first type of plant systematically exhibits a diffusion curve similar to that of other pollen particles from the same plant. Of course, the diffusion curves of two particles are still not exactly identical. Slight variations can appear between two particles, or according to the orientation of the illuminated particle. However, by analyzing a large number of pollen particles of each type, the inventors have obtained a curve representative of the mean diffusion of the particles of each type, associated with uncertainty curves, which can be variable as a function of the angle of diffusion.

When particles with different diffusion curves are measured, it is possible to discriminate between them by performing a measurement of the diffused light, at angular positions chosen so that the diffusion value of the two types of particles represents a difference greater than the standard deviations. However, since the particles that may be present in the air are very diverse, it is impossible to discriminate between all of them with a single measurement.

From the analysis of the diffusion curves of a large number of pollens and other particles, the inventors determined that the measurements of the diffused light carried out in four different angular ranges were sufficient to identify the pollen particles in a vast majority of cases.

Thus, a first photosensitive sensor measuring the diffused light in an angular range comprised between 5° and 25° makes it possible to measure a value of the diffused luminous flux that depends on the size of the particle, and therefore makes it possible to determine this size. This first sensor therefore makes it possible to detect the passage of a particle, and thus to increment a counter performing the counting of the particles, to determine its size and to give the reference value of the diffused luminous flux, which will serve as a basis of comparison for the measurements of the luminous flux diffused at the other angles. It should be noted that this measurement angle for the first photosensitive sensor is chosen so as to be as low as possible, while avoiding receiving the luminous flux directly emitted by the light beam.

Determining the size of the particles makes it possible, in particular, to distinguish the grains of pollen, commonly between 10 and 100 µm in size, from finer particles such as soot or dust. In particular, it has been observed that mineral particles rarely have sizes greater than 10 µm. It also makes it possible to distinguish pollen grains of relatively small size, for example pellitory-of-the-wall pollen grains whose size is approximately 15 µm, from larger pollen grains, such as, for example, corn pollen grains, whose size is about 100 µm.

The other photosensitive sensors, positioned to measure the light diffused at other angles, make it possible to measure the luminous flux diffused by the particle when it is illuminated, which can be compared with the luminous flux measured by the first sensor, placed at the lowest angle.

Thus, in the embodiment shown, the second sensor, positioned to measure the light diffused in an angular zone located around 60°, the third sensor, positioned to measure the light diffused in an angular zone located around 125°, and the fourth sensor, positioned to measure the light diffused in an angular zone located around 157°, make it possible to determine the luminous flux diffused by a particle, in the direction in which they are positioned. It is then possible to determine the ratio between the luminous flux diffused in each of these directions and the luminous flux diffused at 15°, and to compare these ratios with the diffusion curves of the different types of particles of comparable size, to determine which curves these ratios come closest to.

Thus, the combination of the measurements in these four angular zones makes it possible, in a large number of cases, to identify the nature of a pollen particle. It should be noted that it is particularly important for one of these sensors to be located in an angular zone comprised between 150° and 175°, and more advantageously between 150° and 160°. Indeed, the inventors have determined that several particles, in particular of pollen, exhibited very similar diffusion curves for diffusion angles of less than 150°, but which clearly diverged for diffusion angles of between 150° and 160°. A photosensitive sensor located in this angular zone therefore makes it possible to determine the ratio between the luminous flux diffused in this angular zone and the luminous flux diffused at 15°, in order to distinguish the particles whose diffusion curve is close below 150°.

These data measured by the detector 2 are transmitted to the computer 5 of the detection device 1, which compares, during the illumination of each particle, the values of the diffused luminous flux measured by each of the four photosensitive sensors with diffused luminous flux data typical for each type of pollen, which are stored in the database 4. In a large number of cases, this comparison enables the computer 5 to determine the nature of the grain of pollen that has been illuminated.

In some cases, however, this comparison is insufficient to determine the nature of the pollen grain with a sufficient level of reliability. This can happen, for example, when two different types of pollen have very similar curves in the directions of diffusion in which the luminous flux is measured, and the values measured for a particle are likely to correspond to several types of pollen.

To allow the identification of the illuminated particle, the detection device 1 comprises a set of meteorological sensors 3. In the embodiment shown, this set of meteorological sensors 3 comprises a thermometer 31, a barometer 32, a hygrometer 33, an anemometer 34, a rain gauge 35 and a light sensor 36. In other embodiments, the set of meteorological sensors 3 can comprise fewer sensors, or other types of sensors. An efficient, compact and inexpensive set of meteorological sensors may thus consist of only a thermometer, a barometer and a hygrometer.

The detection device 1 also advantageously comprises a clock 37, making it possible to know the time and the date, hereinafter called dating data, and geolocation equipment 38.

The meteorological sensors, the clock and the geolocation equipment 38 can transmit the data that they measure to the computer 5. This computer 5 can compare these data with reference data stored in the database 4, such as reference data concerning the appearance conditions of the different types of pollen. It can, for example, compare the dating data supplied by the clock 37 with a schedule of the appearance of the different types of pollen. This schedule can itself be chosen by the computer 5, from among several available schedules, depending on the geolocation data measured by the geolocation equipment 38, so that this schedule best corresponds to the climatic conditions, and to the known types of plants in the zone in which the detection device 1 is located.

The computer 5 can also compare the meteorological data measured by the sensors of the set of meteorological sensors 3 with known data concerning the appearance of each type of pollen. It is for example known, in particular through the study by K. Laaidi, M. Laaidi and J.-P. Besancenot, 1997: POLLENS, POLLINOSES ET MÉTÉOROLOGIE, La Météorologie 8e serie-no. 20, 41-56, that birch pollen appears in Paris when the sum of 260° C. days above 3° C. is accumulated after February 11. The database 4 advantageously contains such information resulting, in particular, from scientific publications.

The comparison, by the computer 5, of this information and the measurements obtained from the set of environmental sensors 3 advantageously makes it possible to determine a probability of appearance of each type of pollen. Thus, in the case where the illumination of a particle leads to the measurement, by the pollen detector 2, of diffused luminous flux values that may correspond to several types of pollen, the probability of appearance associated with each of these types of pollens makes it possible, in a large number of cases, to determine the type of this particle with a sufficient level of reliability.

Advantageously, the computer 5 can thus comprise a program making it possible to take into account at once the information from the photosensitive sensors, the meteorological sensors, the clock and the geolocation equipment, to determine the nature of the detected pollen particle.

According to an advantageous embodiment, the computer 5 can be equipped with an automatic learning program, usually referred to as a "Machine Learning" program, capable of identifying correlations between the data measured by different sensors of the detection device 1 and the type of pollen particles detected by the detector 2. Such an automatic learning program can define identification rules making it possible to accelerate, and to make more reliable, the identification of the particles detected by the detector 2. It can also make it possible, in certain cases, to predict the appearance of certain types of pollen, even before their detection by the detector 2, from data measured by the meteorological sensors, the clock 37 and the geolocation equipment 38.

The detection device 1 is advantageously equipped with a communication module 6. This module allows information to be sent to a remote server on the type and quantity of pollen grains detected. The remote server can thus collect pollen measurement data in real time at the place where the detection device 1 is placed.

In an advantageous embodiment, the remote server can also communicate meteorological data to the detection device 1, for example meteorological forecast data, and pollen measurement or presence data measured by other pollen detection devices, of the same type or of a different type. Such data can advantageously be used by the computer 5, in the same way as the data coming from the sensors of the detection device 1, to determine the probability of appearance of each type of pollen, in order to contribute to the identification of a particle illuminated in the sensor 2 or to predict the appearance of pollen.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A device for detecting a presence of pollen in air, comprising:
    a measuring chamber isolated from external light,
    means for driving an air flow through said measuring chamber,
    a light source emitting a light beam in a direction of propagation through said air flow, into said measuring chamber,
    at least four photosensitive sensors configured to measure a luminous flux diffused by said illuminated air flow, including:
        a first sensor measuring said luminous flux diffused in a direction forming an angle of between 5° and 25° with said direction of propagation;
        a last sensor measuring said luminous flux diffused in a direction forming an angle of between 150° and 175° with said direction of propagation;
        at least two sensors each measuring said luminous flux diffused in a direction forming an angle of between 25° and 150° with said direction of propagation;
    a clock,
    at least two meteorological sensors, and
    at least one computer configured to determine a nature of a pollen particle present in the air from data measured by said photosensitive sensors, said clock and said meteorological sensors.

2. The detection device according to claim 1, wherein said at least four photosensitive sensors configured to measure the luminous flux diffused by said illuminated air flow are limited to no more than four photosensitive sensors.

3. The detection device according to claim 1, wherein said first sensor measures said luminous flux diffused in a direction forming an angle comprised between 5° and 20° with said direction of propagation.

4. The detection device according to claim 1, wherein said last sensor measures said luminous flux diffused in a direction forming an angle comprised between 150° and 160° with said direction of propagation.

5. The detection device according to claim 1, further comprising a database comprising luminous flux data diffused by pollen of different types, said computer being able to compare said data with the luminous fluxes measured by said photosensitive sensors.

6. The detection device according to claim 1, further comprising a database comprising data relating to a probability of an appearance of pollen as a function of a date and meteorological parameters, said computer being configured to compare said data with data measured by said clock and said meteorological sensors.

7. The detection device according to claim 1, further comprising at least one geolocation device and a database comprising data concerning a probability of an appearance of pollen as a function of geolocation, said computer being configured to take said geolocation into account to determine the nature of a pollen particle.

8. The detection device according to claim 1, wherein said meteorological sensors comprise at least two sensors chosen from:
    a thermometer,
    a barometer,
    a hygrometer,
    an anemometer,
    a rain gauge, and
    a light sensor.

9. The detection device according to claim 8, wherein said meteorological sensors comprise at least:
    a thermometer,
    a barometer, and
    a hygrometer.

10. A method for detecting a presence of pollen in air, comprising:
    a step of illuminating an air flow circulating in a measuring chamber, by a luminous flux oriented in a direction of propagation;
    a step of measuring the luminous flux diffused by said illuminated air flow, in at least four directions, including a direction forming an angle of between 5° and 25° with said direction of propagation, a direction forming an angle of between 150° and 175° with said direction of propagation, and at least two directions each forming an angle of between 25° and 150° with said direction of propagation;
    a step of determining, by a computer, a nature of a pollen particle present in said air flow, from the diffused luminous flux data measured in said measuring step, dating data and meteorological data.

* * * * *